United States Patent [19]

Burr et al.

[11] 4,069,705
[45] Jan. 24, 1978

[54] ANALYSIS OF MATERIALS

[75] Inventors: Kenneth John Burr; Stephen Ross Holland, both of St. Austell, England

[73] Assignee: English Clays Lovering Pochin & Co. Ltd., St. Austell, England

[21] Appl. No.: 679,568

[22] Filed: Apr. 23, 1976

Related U.S. Application Data

[63] Continuation of Ser. No. 612,750, Sept. 12, 1975, abandoned, which is a continuation of Ser. No. 430,530, Jan. 3, 1974, abandoned.

[30] Foreign Application Priority Data

Jan. 11, 1973    United Kingdom .................. 1623/73

[51] Int. Cl.$^2$ .............................................. G01N 9/18
[52] U.S. Cl. ...................................... 73/61 R; 73/451
[58] Field of Search ............ 73/61 R, 61.4 R, 432 PS, 73/433, 447, 448, 451, 452, 453; 137/91

[56] References Cited

U.S. PATENT DOCUMENTS

| | | | |
|---|---|---|---|
| 2,543,522 | 2/1951 | Cohen | 73/452 X |
| 2,717,079 | 9/1955 | Levi | 137/91 X |
| 2,782,926 | 2/1957 | Saxe | 73/433 X |
| 3,439,800 | 4/1969 | Tonjes | 73/432 PS X |
| 3,545,281 | 12/1970 | Johnston | 73/432 PS |
| 3,690,183 | 9/1972 | Livingood | 73/432 PS |
| 3,813,947 | 6/1974 | Hinde | 73/432 PS |

*Primary Examiner*—Charles A. Ruehl
*Assistant Examiner*—Joseph W. Roskos
*Attorney, Agent, or Firm*—Larson, Taylor and Hinds

[57] ABSTRACT

There is disclosed a device suitable for obtaining from a fluid mixture of first and second component materials a quantity thereof which contains a fixed weight of said first component material, and an apparatus for determining the proportion by weight of particles of a particulate solid material in suspension in a liquid which are larger than a given size. The apparatus comprises (i) means for delivering a quantity of the suspension containing a fixed weight of particulate solid material, (ii) means for separating from said quantity of suspension substantially all the solid particles larger than said given size; and (iii) means for determining the weight of said solid particles which are larger than said given size.

8 Claims, 6 Drawing Figures

ANALYSIS OF MATERIALS

This is a continuation of application Ser. No. 612,750 filed Sept. 12, 1975 now abandoned; which is a continuation of Ser. No. 430,530 filed Jan. 3, 1974, now abandoned.

BACKGROUND OF THE INVENTION

This invention relates to the analysis of materials and, more particularly but not exclusively, is concerned with apparatus for use in determining the proportion of solid particles larger than a specified size in a fluid mixture consisting of a suspension of a particulate solid material in a liquid, and with a device which inter alia is suitable for use in such apparatus.

In many industries which produce or process a particulate solid material it is often important to ensure that the particule size distribution of the product or material to be processed remains within predefined tolerance limits. It is often especially desirable to control the proportion of coarse, over-size particles in the particulate solid material and, to this end, it is desirable to be able to determine the proportion of particles larger than a given size in a sample of the material and thus in the material itself, in a convenient manner. Frequently, the material concerned is in the form of a slurry or suspension thereof in a liquid, and in order to carry out the desired determination, it is desirable to be able to obtain a sample of the slurry or suspension containing a fixed weight of the particulate solid material.

SUMMARY OF THE INVENTION

According to a first aspect of the present invention there is provided a device suitable for obtaining from a fluid mixture of first and second component materials a quantity thereof which contains a fixed weight of said first component material, the density of said second component material being known and the mixture containing the two component materials in unknown proportions, which device comprises a container, a float, and means for indicating, during use of the device, when the float has reached a fixed height above the bottom of the container, the relative shape of the container and the float being such that, when a volume of the fluid mixture containing said fixed weight of the first component material has been introduced into the container, the float, over a range of proportions of said first and second component materials, will float at said fixed height above the bottom of the container independently of the relative proportions, within said range of proportions, of the first and second component materials in the fluid mixture.

Figures 1, 2:
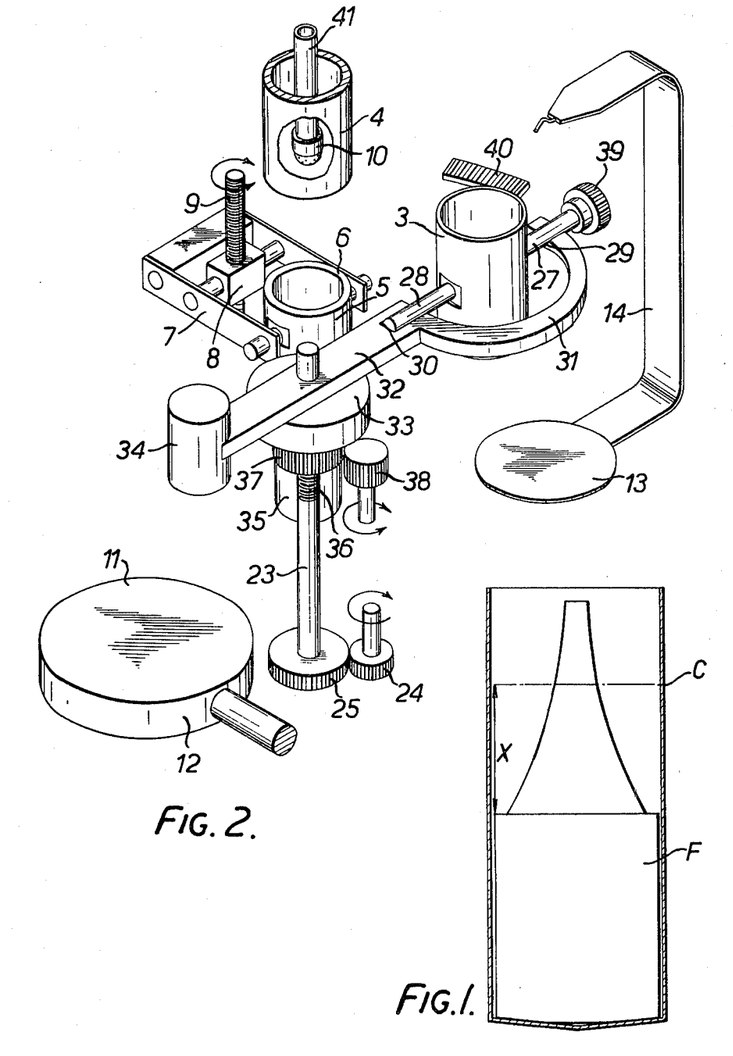
FIG. 1 shows diagrammatically a device according to the first aspect of the present invention.
FIG. 2 is a diagrammatic, perspective view of one embodiment of apparatus according to the second aspect of the present invention.

In order to show how a container and a float can be constructed and shaped relative to each other so as to provide the desired relationship, reference should now be made to FIG. 1 of the accompanying drawings in which one embodiment of a device according to the invention is shown diagrammatically. The device comprises a cylindrical container, which is identified generally as C, and a float, which is identified generally as F, the float consisting of a cylindrical lower portion and a "shaped" upper portion, If it is assumed, for the purpose of illustration only, that the fluid mixture of first and second component materials consists of a suspension of fine particulate solid material (the first component) in a suspending liquid (the second component) and that:

A is the known cross-sectional area of the cylindrical container;

$a_x$ is the cross-sectional area of the float at a height $x$ above the junction of the cylindrical lower portion and the shaped upper portion of the float;

$v_c$ is the known volume occupied by the cylindrical lower portion of the float;

$D_x$ is the density of a fluid mixture in which the float floats with the surface of the fluid mixture at a height $x$ above the junction of the cylindrical lower portion and the shaped upper portion of the float $D_{max}$ is the known density of the fluid mixture in which the float floats with the surface of the fluid mixture level with the junction between the cylindrical lower portion and the shaped upper portion of the float, i.e. when $x = 0$;

$v_s$ is the known volume of the fluid mixture of density $D_{max}$ in the container when the float floats and is at the fixed height above the bottom of the container;

$D_f$ is the known density of the second component, i.e. the suspending liquid;

$D_s$ is the density of the first component, i.e. the fine particulate solid; and W is the weight of said first component per unit volume of fluid mixture then:

the density of the fluid mixture $D_x$ is equal to the weight of the first component per unit volume of the fluid mixture plus the weight of the second component per unit volume of the mixture, i.e.

$$D_x = W + (1 - \frac{W}{D_s}) D_f \text{ and hence } W = \frac{D_x - D_f}{1 - D_f/D_s}$$
$$= C(D_x - D_f)$$

where $C$ is a constant for the particular components of a fluid mixture. The volume of the fluid mixture required to contain a fixed weight of solid component is therefore inversely proportioned to $(D_x - D_f)$. If the volume of fluid mixture of density $D_x$ which contains the required fixed weight of solid component floats the float with the level of the fluid mixture at a distance $x$ above the junction of the cylindrical lower portion and the shaped upper portion of the float, then $$v_s + Ax - \int_o^x a_x dx = \frac{K}{D_x - D_f}$$

where $K$ is a constant. When $x = 0$, $D_x = D_{max}$ and $v_s = K/(D_{max} - D_f)$ so that $K = v_s(D_{max} - D_f)$. Substituting for $K$ $$v_s + Ax - \int_o^x a_x dx = \frac{(D_{max} - D_f)}{D_x - D_f} v_s \quad (1)$$

Also, whatever the density of the fluid mixture in which the float is floating the upthrust must always be the same and equal to the weight of the float.

Therefore $$v_c D_{max} = (v_c + \int_o^x a_x dx) \cdot D_x$$

and $$\int_o^x a_x dx = \frac{D_{max} v_c}{D_x} - v_c$$

Differentiating: $$a_x = \frac{D_{max} v_c}{D_x^2} \cdot \frac{dD_x}{dx} \quad (2)$$

-continued

Also by substituting for $\int_0^x a_x dx$ in equation (1)

$$v_s + Ax - \frac{D_{max} v_c}{D_x} - v_c = \frac{(D_{max} - D_f)}{D_x - D_f} \cdot v_s$$

Hence, solving for $D_x$, for the required conditions $$D_x = \frac{D_f(Ax+v_c)+D_{max}(v_c+v_s)+\sqrt{[(Ax+v_c)D_f+(v_c+v_s)D_{max}]^2-4(v_s+v_c+Ax)v_c D_f D_{max}}}{2(v_s+v_c+Ax)} \quad (3)$$

and on differentiating it is found that $$\frac{dD_x}{d_x} = \frac{A}{2(v_c+v_s+A_x)^2} \cdot \left( v_s D_f - D_{max}(v_c+v_s) + \frac{D_f(v_s+v_c A_x)[D_f(v_c+A_x)+D_{max}(v_s-v_c)]}{\sqrt{[D_f(v_c+A_x)+D_{max}(v_c+v_s)]^2-4(v_s+v_c+A_x)v_c D_f D_{max}}} - \right.$$

$$\left. \sqrt{[D_f(v_c+A_x)+D_{max}(v_c+v_s)]^2-4(v_s+v_c+A_x)v_c D_f D_{max}} \right) \quad (4)$$

By substituting (3) and (4) in (2), an expression may be derived for $a_x$ as a function of $x$ and constants $A$, $v_c$, $D_{max}$, $v_s$ and $D_f$, and in this way it is possible to obtain enough information to define the profile of the upper shaped portion of the float.

According to a second aspect of the present invention there is provided an apparatus suitable for determining the proportion by weight of particles of a particulate solid material in suspension in a liquid which are larger than a given size, which apparatus comprises (i) means for delivering a quantity of the suspension containing a fixed weight of particulate solid material, (ii) means for separating from said quantity of suspension substantially all the solid particles larger than said given size; and (iii) means for determining the weight of said solid particles which are larger than said given size.

DESCRIPTION OF THE PREFERRED EMBODIMENTS

In order to obtain consistent results it is advantageous if the device according to the first aspect of the invention is constructed so that the volume $V_c$ is large compared with $V_s$, the latter parameter controlling the volume of the sample of the fluid mixture delivered. The sensitivity of the device is determined also by the cross-sectional area of the shaped portion of the float and the ratio of this area, at its maximum, and the cross-sectional area, $A$, of the container; therefore the values of $A$ and $V_c$ are chosen with these criteria in mind. The mean density of the float (i.e. the ratio: total mass of float/overall effective volume) is chosen having regard to the factors referred to above and to the desired value for $D_{max}$.

Preferably, the container is a generally upright cylindrical vessel. Advantageously the float is made so that its total mass can be changed without changing its overall effective volume. The means for indicating when the float has reached a fixed height above the bottom of the container can be simply a mark at the appropriate place on the side of the container or preferably, a microswitch which is operated by the float when the latter reaches said fixed height so as to cut off the supply of further fluid mixture to the container. When a float, which has been shaped so as to fulfill the equations given above, reaches the fixed height above the bottom of the container as a result of the addition of the fluid mixture to the container, the volume of the fluid mixture in the container will, for a range of proportions of the first and second component materials, contain the same weight of the first component material (e.g. the fine particulate solid) irrespective of the relative proportions of the first and second component materials in the fluid mixture.

The means for delivering a quantity of the suspension containing a fixed weight of the particulate solid material advantageously comprises a device in accordance with the first aspect of the present invention.

Preferably, the apparatus also comprises means for discharging therefrom the solid particles larger than said given size after the weight thereof has been determined.

Advantageously, the apparatus according to the second aspect of the invention is constructed so that its operation can be initiated and controlled automatically.

Generally, it is convenient if the means for separating substantially all the solid particles larger than a given size from the delivered quantity of the suspension, and the means for determining the weight of said solid particles larger than said given size, are disposed at different stations, or locations, of the apparatus.

The means for separating from the delivered quantity of suspension substantially all the solid particles larger than a given size can be a sieve of an appropriate mesh size which is preferably mounted in a suitable housing.

The means for determining the weight of the solid particles larger than a given size can comprise means for drying the solid particles and means for weighing the dried solid particles.

Preferred embodiments of apparatus according to the second aspect of the present invention comprise (a) a device in accordance with the first aspect of the invention for obtaining a quantity of suspension containing a fixed weight of a particulate solid material, (b) a sieve for separating from said quantity of suspension substantially all the solid particles larger than a given size, (c) means for drying the solid particles retained on said sieve, (d) means for weighing the dried solid particles contained on said sieve, and (e) means for discharging from the apparatus said solid particles whose weight has been determined.

It is advantageous for the apparatus to be constructed so that the sieving, drying and weighing operations can be performed within a housing at three separate stations, or locations, each operation being performed with the over-size solid material held on the sieve. To this end, an indexing unit is provided to locate the sieve and its housing accurately in each of the three stations or positions.

The means for drying the solid particles is advantageously a radiant heater; and if an electrical heating element is used for this purpose, the heating element should be protected from splashes of the suspension by, for example, a temperature-resistant, heat-conducting shield.

The means for weighing the solid particles retained on the sieve preferably comprises a balance arm which is counterbalanced by a force which is exactly equal and opposite to the weight of the sieve and its housing when they are clean and empty, and means for generating an analogue signal directly proportional to the degree of out-of-balance when the weight of the sieve and any solid particles held thereon together with that of the housing for the sieve are applied to the end of the balance arm. In this way the analogue signal can be made to be directly proportional to the weight of solid particles on the sieve and hence also to the weight fraction of oversize particles in the solid material. The analogue signal obtained is preferably applied to means for giving a visual indication or record of the weight of solid particles on the sieve expressed as a percentage of the original total weight of solids in the sample of suspension. The analogue signal obtained may also be applied to an on-line controlling unit when the apparatus is used as part of control apparatus for a continuous process.

For a better understanding of the invention, and to show how the same may be carried into effect, reference will now be made by way of example to the accompanying drawings in which.

The embodiment of apparatus according to the second aspect of the invention, which is shown in FIGS. 1, 2, 3 and 4 of the accompanying drawings, comprises the following principal components:

a. a device according to the first aspect of the present invention for obtaining a quantity of a fluid mixture containing a known weight of a first component material;

b. a sieve in a housing;

c. an indexing unit for locating the sieve and its housing at (i) a sieving position, (ii) a drying position, and (iii) a weighing position;

d. a sieve-washing system;

e. an infra-red dryer;

f. an electrical weighing unit; and g. an electronic programme controller.

In more detail, there is shown in FIGS. 1, 2, 3 and 4 an apparatus which includes a device (FIG. 1) according to the first aspect of the invention, the latter comprising a container 1, a float 2, and means S for indicating when the float has reached a fixed height above the bottom of the containers. The float is displaced when a quantity of a fluid mixture of two component materials enters the container. The profile of the float is such that the uppermost part of the float reaches a fixed height above the bottom of the container when the quantity of fluid mixture delivered into the container contains a fixed weight of the first component material, e.g. a particulate solid material. When the uppermost part of the float reaches the fixed height, it operates the microswitch S which causes an inlet to close thereby stopping the delivery of the fluid mixture into the container 1. The float 2 employed in this embodiment of the device according to the first aspect of the invention is designed to function when the specific gravity of the fluid mixture is in the range of from 1.040 to 1.200; at the upper limit, when the float is floating the bottom of the shaped portion of the float is level with the surface of the fluid mixture, and at the lower limit, the container 1 is filled to capacity when the float is floating. Associated with the container 1 are water jets (not shown) which, in use, direct rinsing water onto the top of the float and across the bottom of the container immediately after the container has been emptied in order to ensure that no residue is left therein.

Figure 3:
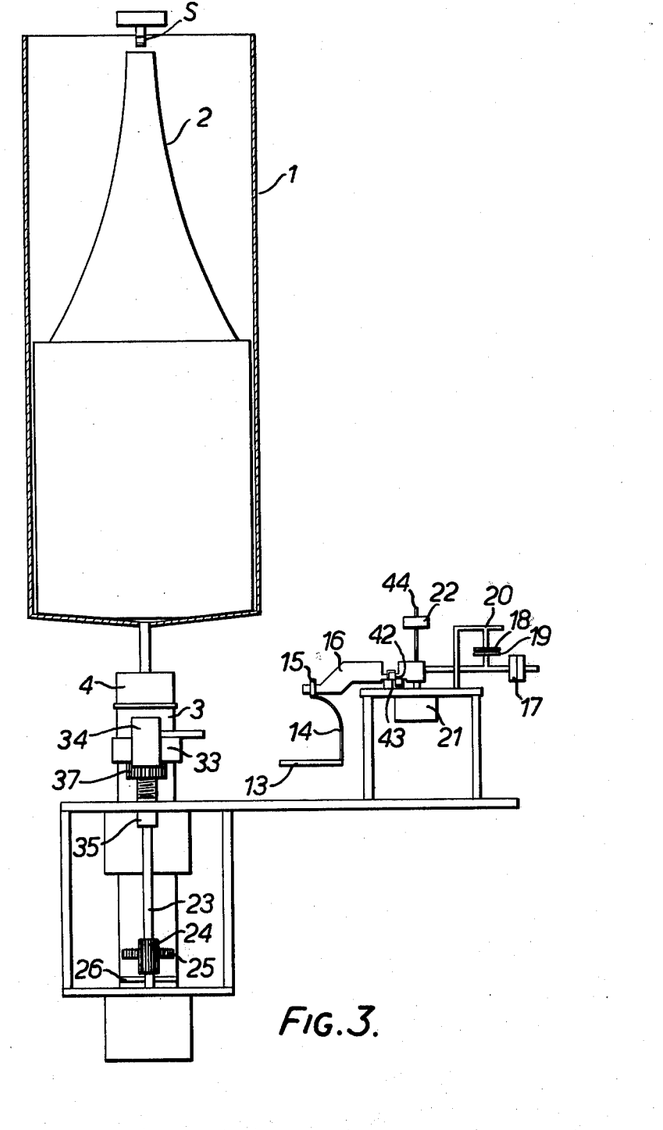
FIG. 3 is a diagrammatic section taken through the embodiment shown in FIG. 2.
Figure 4:
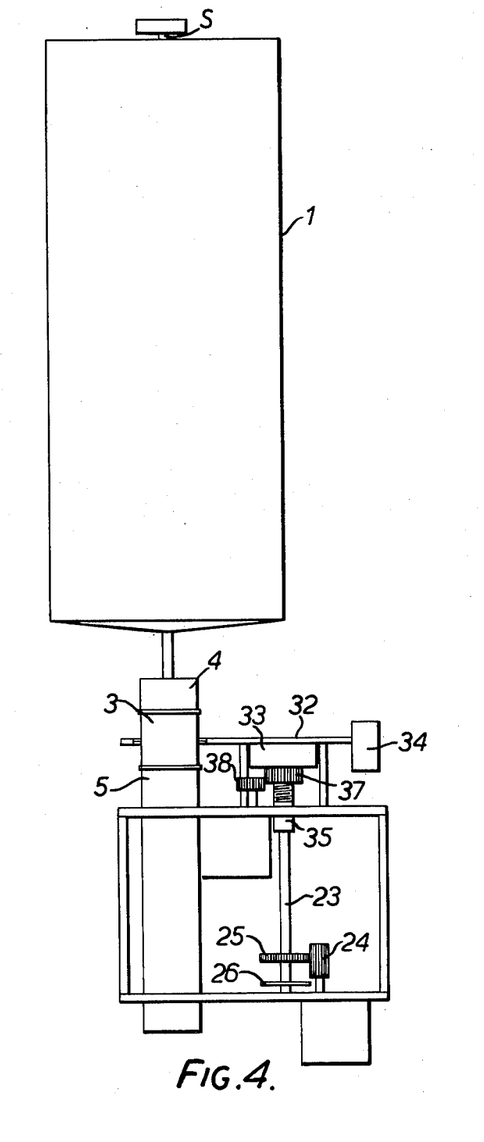
FIG. 4 is a diagrammatic section taken through the embodiment shown in FIG. 2 at right angles to the section of FIG. 3.

A sieve of standard mesh size, which is in the form of a circular disc (of diameter 1¾ inches) cut from a No. 300 mesh B.S. sieve cloth, is mounted in a cylindrical sieve housing 3. The sieve housing 3 is provided with two horizontally disposed round bars 27 and 28 which rest in slots 29 and 30 of a C-shaped portion 31 of a bar 32. The bar 32 is rigidly fixed to a hub 33, and is provided with a balancing weight 34. The hub 33 and bar 32 are provided with a keyway which co-operates with a key on a central vertical shaft 23 of the indexing unit to permit vertical movement on the shaft but no rotational movement relative to the shaft. The hub 33 rests on a toothed wheel 37 which co-operates with a threaded portion 36 of the central vertical shaft 23 the toothed wheel 37, in use, co-operates with a pinion wheel 38 which is driven clockwise or counter-clockwise by an electric motor in order to raise or lower the hub and thus the sieve housing. A microswitch (not shown) is provided to de-energise the electric motor when the hub has descended sufficiently to deposit the sieve housing on a balance pan 13 which forms part of the weighing unit so that bars 27 and 28 are clear of the slots 29 and 30, respectively. The subsequent raising operation is controlled on a time basis.

The indexing unit comprises the central vertical shaft 23 which runs in a bearing 35 and which can be rotated by means of an electric motor (not shown), driving through an electrically actuated clutch (not shown), and pinion wheels 24 and 25. When the shaft is rotated through 90°, the sieve and its housing is advanced from the sieving position to a drying position; rotation of the shaft through a further 180° advances the sieve and its housing from the drying position to a weighing position. The desired position of the sieve housing is determined by means of a notched cam 26 mounted on a central vertical shaft, which cam co-operates with a microswitch (not shown). In use, an electric motor rotates continuously and the sieve housing is advanced by engaging the clutch until the arm of the microswitch slips into a notch on the cam, thus disengaging the clutch.

When in the sieving position, the sieve housing 3 is clamped between two cylinders 4 and 5 faced with rubber sealing rings 6. The upper cylinder 4 is rigidly fixed while the lower cylinder 5 is pivotally mounted in a frame-work 7 which can be raised and lowered by means of a tapped block 8 which co-operates with a theaded rod 9 which, in turn, can be driven clockwise or counter-clockwise. The upper cylinder 4 contains a rose 10 which is supplied with washing water at a pressure of approximately 65 p.s.i. through a conduit 41.

When in the drying position, the sieve is acted upon by an infra-red heater 11 which comprises an electric heating element disposed in a cylindrical housing 12 formed of fused silica. The heating element is capable of drying any solid material retained on the sieve within a time of approximately 1 to 5 minutes, depending upon the nature of the liquid in which the solid material was suspended.

When in the weighing position, the sieve is received by the weighing unit which comprises the balance pan 13 rigidly fixed to a suspending arm 14 which carries, at its upper end, an agate knife edge 15. The agate knife edge rests on one end of a balance arm 16. The balance arm 16 is pivoted on pairs of crossed flexure strips one pair of which is shown at 42 and 43, and carries at its end opposite to the balance pan 13 a pair of counterweights 17 to offset the weight of the balance pan and the empty sieve housing. Balance of the weighting unit is detected electrically by means of a pair of parallel capacitor plates 18 and 19, the upper one of which, 18, is fixed to a rigid support 20, and the lower one of which, 19, is mounted on the balance beam. Changes is capacitance between the two plates are converted into changes in current by mens of a capacitance transducer and the current is passed through a moving coil of a force motor 21 in which the coil moves in a constant magnetic field. The force thus generated is always that required to return the balance beam to the balance condition. If the beam is initially balanced with zero current when the sieve housing on the balance beam is empty, then the current flowing through the coil of the force motor will be directly proportional to the weight of material on the sieve, since the force generated by the force motor is directly proportional to the current flowing in the moving coil. A second winding on the moving coil of the force motor is used for fine adjustment of the balance for zeroing purposes and is fed from a stabilised variable current source. A sensitivity adjusting weight 22, capable of upward and downward movements on a threaded rod 44, is also provided. The balancing current is passed through a resistor of suitable value and a digital voltmeter connected across this resistor is calibrated to indicate directly the percentage by weight of solid particulate material retained on the sieve. The reading of the digital voltmeter is retained until the next weighing is made. A memory device, e.g. a potentiometer driven by a servo-motor, can be employed if it is required to retain the measured quantity in analogue form during the duration of a cycle.

After each operational cycle, the sieve housing 3 is inverted by means of a pinion wheel 39 carried on bar 27 and meshing with a rack 40. The number of teeth on the rack is such as to invert the sieve housing through 180°.

A programme controller (not shown), which utilises, for example, solid-state logic units, enables the sequence of operations of the apparatus to be controlled automatically, if desired.

In use, the apparatus described above performs the following sequence of operations in the course of a typical cycle:

1. A fluid mixture consisting, for example, of a particulate solid material in suspension in a liquid is introduced into the container 1 until the float 2 rises to a fixed height at which its top contacts the arm of the microswitch S and thereby brings about an interruption in the flow of the fluid mixture. A fixed weight of particulate solid material will now be present in the container 1.

2. When (a) the sieve housing containing the sieve is in the sieving position, (b) the surface of the sieve is clean and (c) the two clamping cylinders 4 and 5 are in place, the quantity of fluid mixture containing the fixed weight of particulate solid material is allowed to flow from the container 1 through the sieve, the flow being assisted by washing water supplied by the rose 10. Any residue from the previous operational cycle adhering to the underside of the sieve is washed away during this operation.

3. The inside of the container 1 is washed clean of residue by means of the water jets and such residue is also transferred to the sieve housing.

4. The sieve housing is unclamped by lowering the lower clamping cylinder 5.

5. The sieve housing is advanced to the drying position by rotating the shaft 23 and bar 32 through 90°.

6. The sieve housing is retained in the drying position for approximately 3 minutes where infra-red heater 11 operates to dry completely, by radiation and convection, the solid material retained upon the sieve.

7. The sieve housing is advanced to the weighing position by rotating the shaft 23 and the bear 32 through 180°.

8. The sieve housing is gently lowered onto the balance pan 13 by lowering the hub 33 by means of the pinion wheel 38 and toothed wheel 37. The bar 32 is detached from the sieve housing which is left standing on the balance pan.

9. The weighing unit is automatically balanced by means of the capacitor plates 18 and 19, the capacitance transducer and the force motor 21. The balancing current is applied across the resistor connected to the digital voltmeter which indicates and records the percentage by weight of solid particulate material retained on the sieve with respect to the known weight of solid particulate material contained in the sample of fluid suspension poured onto the sieve from the container.

10. The bar 32 is raised by means of the pinion 38 to pick up the sieve housing.

11. The sieve and its housing are advanced to the sieving position by rotating the bar 32 through 90°. During this operation the sieve housing is inverted by means of the pinion 39 and the rack 40, thus discharging the weighed residue.

12. The sieve housing is clamped in the sieving position by raising the lower clamping cylinder 5.

The cycle is now complete and the apparatus is ready to begin a new cycle.

The embodiment of the apparatus of the invention described above and shown in FIGS. 1, 2, 3 or 4 of the accompanying drawings was designed to measure the proportion by weight of solid particulate material of a size greater than 53 microns (No. 300 mesh B.S. sieve) in a sample of kaolin clay in suspension in water, the proportion by weight of solid particulate material greater than the given size being within the range of from 0.002 to 0.100% by weight based on the total weight of dry solid particulate material. The device according to the invention was constructed and shaped so that the sample taken for each determination contained 480g. of solid particulate material; therefore the weight of residue which can be measured by the described embodiment of the apparatus is in the range of from 10 to 480 mg. The operational cycle of the apparatus is continuously repeatable and takes approximately nine minutes.

Figure 5:
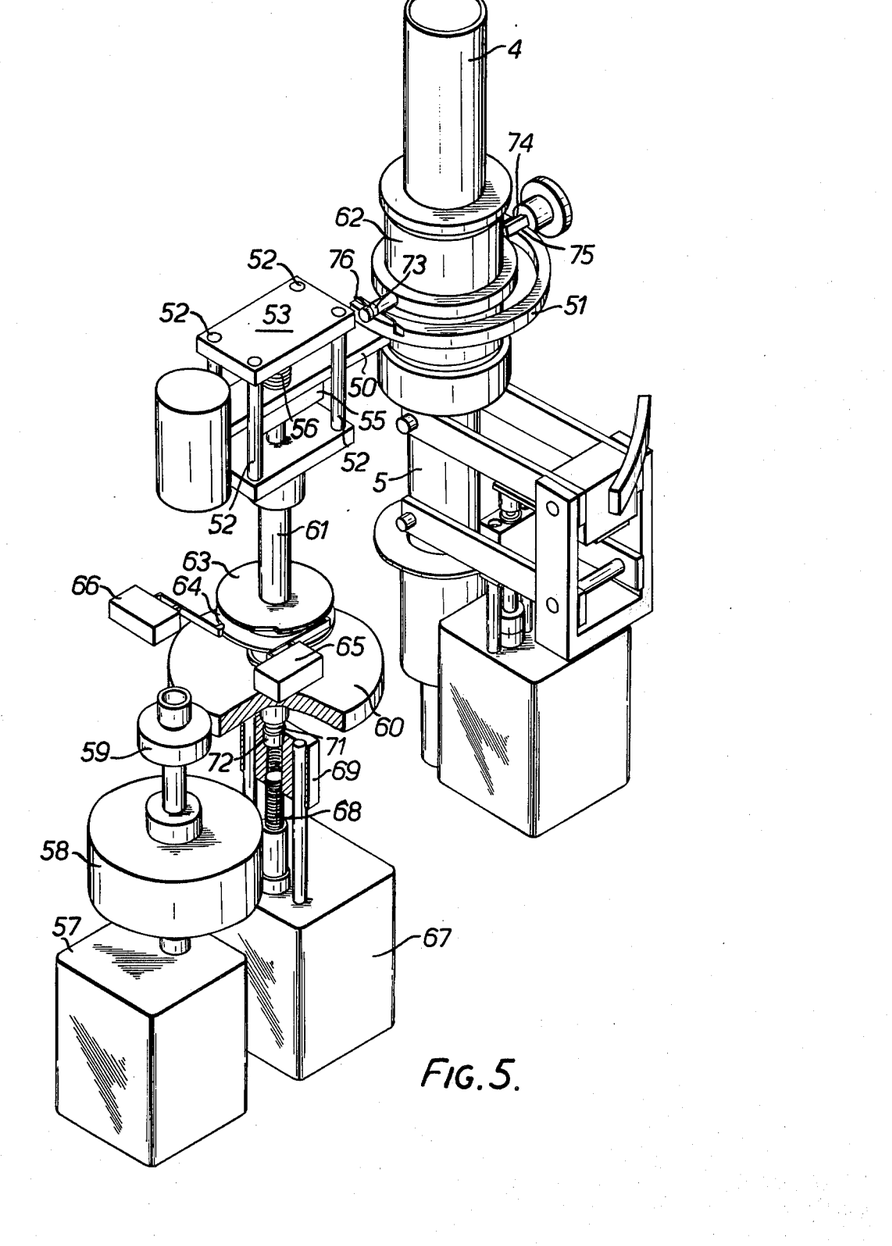
FIG. 5 is an isometric view of a modified form of part of the apparatus shown in FIGS. 1, 2, 3 and 4.
Figure 6:
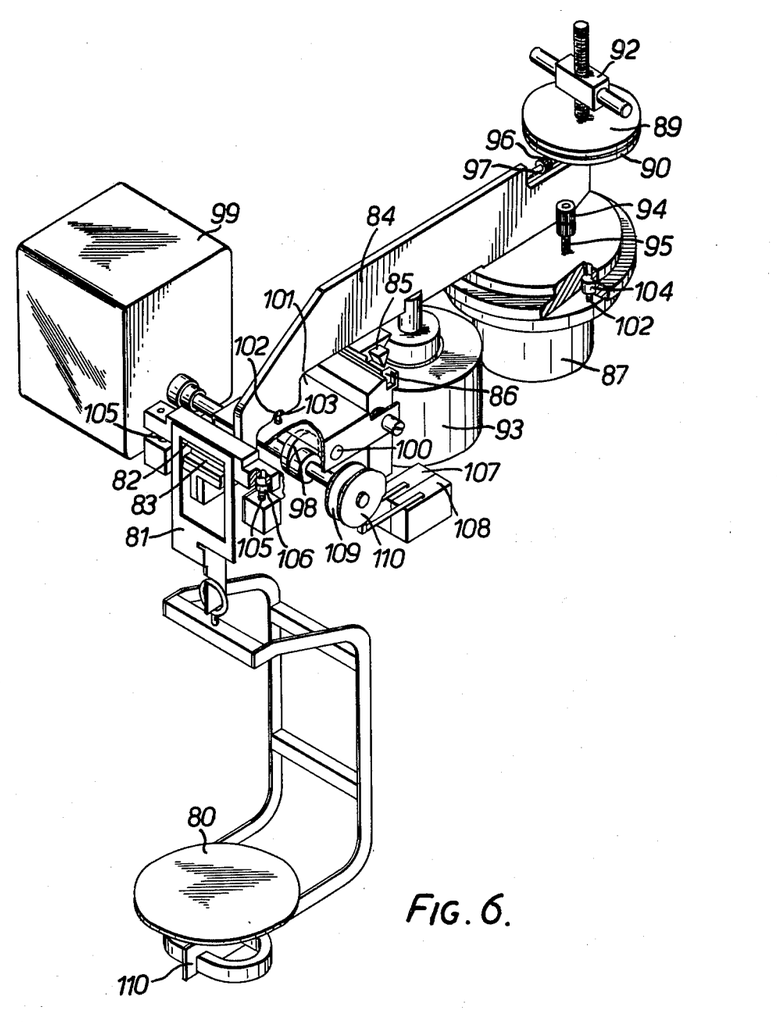
FIG. 6 is an isometric view of a modified form of another part of the apparatus shown in FIGS. 1 to 4.

Referring now to FIGS. 5 and 6 of the accompanying drawings there are shown alternative arrangements for the indexing unit and the electrical weighing unit. In FIG. 5, which shows an alternative arrangement for the indexing unit, a bar 50, on which is mounted a C-shaped support 51, is held in a cage formed by pillars 52 and top and bottom plates 53 and 54, respectively, and is biased against a platform 55 by a compression spring 56. The cage, and the bar 50, may be rotated by means of a motor 57 which acts through clutch 58, gears 59 and 60, and the outer shaft 61 of a concentric shaft system. The sieve housing 62 which rests in the C-shaped support 51 may thus be moved round to the required positions for the sieving, drying and weighing operations. Cams 63 and 64 which operate microswitches 65 and 66, control the positions at which the rotation stops by acting to de-energise the clutch.

The raising and lowering of bar 50 is accomplished by the rotation of the shaft of a motor 67 which, by means of a threaded rod 68, moves bock 69 up or down, depending on the direction of rotation. The inner shaft 70 of the concentric shaft system has a conical end 71 which rests in a hardened conical insert 72 in block 69. The upper end of shaft 70 is fixed to platform 55, so that vertical motion of block 69 is transmitted through shaft 70 and platform 55 to bar 50.

The sieve housing 62 is provided with a shaft 73 having a waisted portion and with a shaft 74 having two flat portions 75. The sieve housing is located laterally by the waisted portion of shaft 73 engaging with a V-shaped notch in a plate 76 and rotationally by the flat portions 75 engaging in a V-shaped notch in the outer end of the C-shaped support 71.

In FIG. 6, which shows a modified weighing unit, a balance includes a balance pan 80 suspended on a suspending arm 81 which carries at its upper end an agate plane 82. When the balance is in operation the plane rests on an agate knife edge 83 fixed to the end of a balance arm 84. The balance arm pivots 84 about an agate knife edge 85, which rests on an agate plane 86, and is counterbalanced by a weight 87 to offset the weight of the balance pan and empty sieve housing. Balance of the weighing unit is detected electrically by means of a pair of parallel capacitor plates 89 and 90, the upper one of which, 89, is fixed to the rigid support 92, and the lower one of which 90 is mounted on the balance arm. Changes in capacitance between the two plates are converted into changes in current by a capacitance transducer (not shown) and the current thus generated is passed through a first winding of a moving coil of a force motor 93 in which the coil moves in a constant magnetic field. The force thus generated is always that required to return the balance beam to the balance condition. If the beam is initially balanced with zero current when the sieve housing on the balance beam is empty, then the current flowing through the coil of the force motor will be directly proportional to the weight of material on the sieve, since the force generated by the force motor is directly proportional to the current flowing in the moving coil. Arrangements are made to turn off the sample delivery pump during weighing to minimise the effect of vibration on the measurement. A second winding on the moving coil of the force motor is used for fine adjustments of the balance for zeroing purposes and is fed from a stabilised variable current source (not shown). A sensitivity adjusting weight 94 capable of upward and downward movement on a threaded rod 95 is provided and also a coarse balance adjusting weight 96 capable of horizontal movement on a threaded rod 97. The balancing current is passed through a resistor of suitable value, and a digital voltmeter connected across this resistor is calibrated to indicate directly the percentage by weight of solid particulate material retained on the sieve. The reading of the digital voltmeter is retained until the next weighing is made, or the reading may be printed out in digital form, if required. A memory device, e.g. a potentiometer driven by a servo-motor, can be employed if it is required to retain the measured quantity in analogue form during the duration of a cycle.

For that part of the cycle when the sieve housing is not on the balance pan the knife edges 83 and 85 are moved out of contact with their agate planes 83 and 86 respectively, in order to protect the knife edges from undue wear from vibration or suddenly applied loads. This is effected by a cam 98 driven by a motor 99, which cam acts on a rod 100, which is fixed to a pivoted member 101. When the pivoted member 101 is raised by the action of the cam, the balance arm is supported on three hemispherical pins 102 (only two shown) which rest respectively in an agate bearing block 103 having a conical bearing surface, an agate bearing block 104 having a V-shaped bearing surface and an agate bearing block (not shown) having a plane bearing surface in order to give precise three-point location. The suspending arm 81 is supported by two pins 105 which rest on a V-shaped agate block 106 and a conical agate block (not shown) to give precise location. The travel of the cam 98 in both directions of rotation is controlled by two microswitches 107 and 108 which are actuated by two cams 109 and 110 which are fixed to the same shaft as cam 98, the microswitches interrupting the electrical supply to the motor 99.

The beam is released after the sieve housing has been lowered on to the weighing pan and is arrested immediately after the reading has been registered. Any slight pendulum motion of the balance pan occurring when the beam is released, due to the centres of gravity of the balance pan and the load not being coincident, is rapidly damped out by means of an aluminium vane 111 which is fixed to the balance pan and hangs in the gap between two U-shaped permanent magnets (not shown) with poles of opposite polarity at adjacent faces.

We claim:

1. A device suitable for obtaining from a fluid mixture of first and second component materials a quantity thereof which contains a fixed weight of said first component material, the density of said second component material being known and the mixture containing the two component materials in unknown proportions, which device comprises a cylindrical container, a float, and means for indicating, during use of the device, when the float has reached a fixed height above the bottom of the container, the float having a cylindrical lower portion contiguous with an upper portion, the upper portion being shaped so that its cross-sectional area $a_x$ at a height x above the lower portion is defined by the formulae $$a_x = \frac{D_{max} v_c}{D_x^2} \cdot \frac{dD_x}{dx} \qquad (2)$$

$$D_x = \qquad (3)$$

-continued
$$\frac{D_f(A_x + v_c) + D_{max}(v_c + v_s) + }{\sqrt{[(A_x + v_c)D_f + (v_c + v_s)D_{max}]^2 - 4(v_s + v_c + A_x)v_cD_fD_{max}}}{2(v_s + v_c + A_x)}$$

$$\frac{dD_x}{dx} = \frac{A}{2(v_c + v_s + A_x)^2} \cdot \Bigg\{ v_sD_f - D_{max}(v_c + v_s) + \tag{4}$$

$$\frac{D_f(v_s + v_c + A_x)[D_f(v_c + A_x) + D_{max}(v_s - v_c)]}{\sqrt{[D_f(v_c + A_x) + D_{max}(v_c + v_s)]^2 - 4(v_s + v_c + A_x)v_cD_fD_{max}}} -$$

$$\sqrt{[D_f(v_c + A_x) + D_{max}(v_c + v_s)]^2 - 4(v_s + v_c + A_x)v_cD_fD_{max}} \Bigg\}$$

wherein:

$A$ is the known cross-sectional area of the cylindrical container;

$a_x$ is the cross-sectional area of the float at a height $x$ above the junction of the cylindrical lower portion and the shaped upper portion of the float;

$v_c$ is the known volume occupied by the cylindrical lower portion of the float;

$D_x$ is the density of a fluid mixture in which the float floats with the surface of the fluid mixture at a height $x$ above the junction of the cylindrical lower portion and the shaped upper portion of the float $D_{max}$ is the known density of the fluid mixture in which the float floats with the surface of the fluid mixture level with the junction between the cylindrical lower portion and the shaped upper portion of the float, i.e. when $x = 0$;

$v_x$ is the known volume of the fluid mixture of density $D_{max}$ in the container when the float floats and is at the fixed height above the bottom of the container;

$D_f$ is the known density of the second component, i.e. the suspending liquid;

$D_s$ is the density of the first component, i.e. the fine particulate solid; and $W$ is the weight of said first component per unit volume of fluid mixture.

whereby, when a volume of the fluid mixture containing said fixed weight of the first component material has been introduced into the container, the float, over a range of proportions of said first and second component materials, will float at said fixed height above the bottom of the container independently of the relative proportions, within said range of proportions, of the first and second component materials in the fluid mixture.

2. A device as claimed in claim 1, wherein said container is a generally upright cylindrical vessel.

3. A device as claimed in claim 1, wherein said means for indicating when the float has reached a fixed height above the bottom of the container is a switching device which is operated by the float when the latter reaches said fixed height so as to cut off the supply of further fluid mixture to the container.

4. An apparatus, suitable for determining the proportion by weight of particles of a particulate solid material in suspension in a liquid which are larger than a given size, which apparatus comprises (i) a device comprising a cylindrical container, a float, and means for indicating, during use of the device, when the float has reached a fixed height above the bottom of the container, the float having a lower portion contiguous with an upper portion, the upper portion being shaped so that its cross-sectional area $a_x$ at a height $x$ above the lower portion is defined by the formulae $$a_x = \frac{D_{max} v_c}{D_x^2} \cdot \frac{dDx}{dx} \tag{2}$$

$$D_x = \tag{3}$$
$$\frac{D_f(A_x + v_c) + D_{max}(v_c + v_s) + }{\sqrt{[(A_x + v_c)D_f + (v_c + v_s)D_{max}]^2 - 4(v_s + v_c + A_x)v_cD_fD_{max}}}{2(v_s + v_c + A_x)}$$

$$\frac{dD_x}{dx} = \frac{A}{2(v_c + v_s + A_x)^2} \cdot \Bigg\{ v_sD_f - D_{max}(v_c + v_s) + \tag{4}$$

$$\frac{D_f(v_s + v_c + A_x)[D_f(v_c + A_x) + D_{max}(v_s - v_c)]}{\sqrt{[D_f(v_c + A_x) + D_{max}(v_c + v_s)]^2 - 4(v_s + v_c + A_x)v_cD_fD_{max}}} -$$

$$\sqrt{[D_f(v_c + A_x) + D_{max}(v_c + v_s)]^2 - 4(v_s + v_c + A_x)v_cD_fD_{max}} \Bigg\}$$

wherein:

$A$ is the known cross-sectional area of the cylindrical container;

$a_x$ is the cross-sectional area of the float at a height $x$ above the junction of the cylindrical lower portion and the shaped upper portion of the float;

$v_c$ is the known volume occupied by the cylindrical lower portion of the float;

$D_x$ is the density of a fluid mixture in which the float floats with the surface of the fluid mixture at a height $x$ above the junction of the cylindrical lower portion and the shaped upper portion of the float $D_{max}$ is the known density of the fluid mixture in which the float floats with the surface of the fluid mixture level with the junction between the cylindrical lower portion and the shaped upper portion of the float, i.e. when $x = 0$;

$v_s$ is the known volume of the fluid mixture of density $D_{max}$ in the container when the float flloats and is at the fixed height above the bottom of the container;

$D_f$ is the known density of the second component, i.e. the suspending liquid;

$D_s$ is the density of the first component, i.e. the fine particulate solid; and $W$ is the weight of said first component per unit volume of fluid mixture.

whereby, when a quantity of the suspension containing a fixed weight of the particulate solid material has been introduced into the container, the float will float at said fixed height above the bottom of the container independently of the relative proportions of the liquid and particulate solid material in the suspension, (ii) means for separating from said quantity of suspension substantially all the solid particles larger than said given size; and (iii) means for determining the weight of said solid particles which are larger than said given size.

5. An apparatus as claimed in claim 4, wherein said apparatus includes a sieve of a mesh size suitable for separating from said quantity of suspension substantially all the solid particles larger than a given size, means for drying the solid particles retained on said sieve, means for weighing the dried solid particles contained on said sieve, and means for discharging from the apparatus said solid particles whose weight has been determined.

6. An apparatus as claimed in claim 5, wherein said apparatus includes an indexing unit for moving said sieve between a sieving position, a drying position and a weighing position.

7. An apparatus as claimed in claim 5, wherein said means for discharging includes means for inverting said sieve.

8. An apparatus as claimed in claim 5, wherein said sieve is mounted in a housing.

* * * * *